US007239245B2

(12) United States Patent
Kang et al.

(10) Patent No.: US 7,239,245 B2
(45) Date of Patent: Jul. 3, 2007

(54) METHOD AND DEVICE FOR MONITORING POSITION OF RADIOACTIVE MATERIALS IN VEHICLES

(75) Inventors: Kejun Kang, Beijing (CN); Wenhuan Gao, Beijing (CN); Xiaobing Wang, Beijing (CN); Jianmin Li, Beijing (CN); Yu He, Beijing (CN); Yinong Liu, Beijing (CN); Yuanjing Li, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 149 days.

(21) Appl. No.: 10/944,432

(22) Filed: Sep. 17, 2004

(65) Prior Publication Data

US 2005/0105681 A1    May 19, 2005

(30) Foreign Application Priority Data

Sep. 18, 2003    (CN) ................................ 03 1 57354

(51) Int. Cl.
*G08B 17/12*    (2006.01)
(52) U.S. Cl. .................... 340/600; 340/686.1; 340/933; 378/53; 378/57; 378/62; 378/83; 378/87; 378/88; 250/358.1
(58) Field of Classification Search ..................... None
See application file for complete search history.

(56) References Cited

U.S. PATENT DOCUMENTS

| 3,278,747 | A | * | 10/1966 | Ohmart ........................ 378/54 |
| 5,838,759 | A | * | 11/1998 | Armistead .................... 378/57 |
| 2004/0086078 | A1 | * | 5/2004 | Adams et al. ................. 378/57 |
| 2004/0256565 | A1 | * | 12/2004 | Adams et al. ........... 250/358.1 |

* cited by examiner

*Primary Examiner*—Benjamin C. Lee
(74) *Attorney, Agent, or Firm*—Patterson, Thuente, Skaar & Christensen, P.A.

(57) ABSTRACT

A method and device for monitoring the position of radioactive materials in vehicles relates to a technical field of monitoring of radioactive materials. The method comprises following steps: powering on a monitoring device, after initializing, the device automatically enters into background mode to acquire and process gamma and neutron detection data so as to obtain and update a background count rate in real time, and an image surveillance system enters into surveillance state; occupancy detector detects that a vehicle enters into monitoring channel, meanwhile the monitoring device automatically enters into occupancy mode, and performs data acquisition process for gamma and neutron detection under the occupancy mode in accordance with the time required by an alarm algorithm, so as to obtain respective total count rates; speed detector detects the times T1 and T2 for the vehicle when it reaches two points with a distance L, and then calculates out the vehicle's speed V; obtaining an alarm threshold by using a special algorithm on the basis of alarming algorithm, particularly, the background count rate updated in real time, and sending an alarm signal when the total count rate exceeds the alarm threshold; transmitting the alarm signal to the image surveillance system via a control interface to notify it of starting to record, meanwhile sending an alarm command to an audio and visual alarm system to inform it of giving out an alarm; with the help of the results of radioactivity detection, speed detection and image capturing, a local computer specifies the position where the radioactive material(s) locate(s) with methods of horizontal and vertical positioning. The present invention can easily and quickly specify the very vehicle and the exact position the radioactive material(s) locate(s) so that the radioactive material(s) can be conveniently isolated and processed subsequently. In this way, time spent on detection has been greatly reduced and lots of human power has been saved.

7 Claims, 5 Drawing Sheets

METHOD AND DEVICE FOR MONITORING POSITION OF RADIOACTIVE MATERIALS IN VEHICLES

RELATED APPLICATION

This application claims priority to Chinese Application No. 03157354.1 filed Sep. 18, 2003.

FIELD OF THE INVENTION

The present invention relates to a the field of monitoring of radioactive materials, especially to a method and device for monitoring the position of radioactive materials in vehicles.

BACKGROUND OF THE INVENTION

In the existing techniques, e.g., the train radioactive materials monitor YANTAR-1/2ZH of Aspect Corporation, monitoring of gamma rays or/and neutron rays is (or are) realized by detecting the abnormal variation of the system's count rate caused by the gamma rays or/and neutron rays radiated by the radioactive materials. However, this kind of device can not provide position information on where the radioactive materials are located. Once it has been determined that a vehicle is loaded with radioactive material(s), an inspection of the vehicle may be required in order to locate the radio active material. In practice, some containers under monitoring are as long as 18 meters (trains are longer), or can have multiple sections or storage compartments. Thus, individual inspection of the vehicles can require significant time and/or human resources.

SUMMARY OF THE INVENTION

To overcome the disadvantages in existing techniques mentioned above, the present invention provides a method and device for monitoring the position of radioactive materials in vehicles. The present invention, with the help of the techniques of speed detection and image surveillance, specifies the position of the vehicles in which the radioactive material(s) lie(s) so as to find the radioactive material(s) in vehicles conveniently and quickly.

To reach the object mentioned above, the following technical solution is adopted in the present invention.

Referring to FIG. 1, a method for monitoring the position of radioactive materials in vehicles comprises the steps of:

Powering on the monitoring device. After initializing, the device automatically enters into a background mode to acquire and process gamma and neutron detection data so as to automatically update the reference background radiation intensity at least every 100 seconds. Additionally, an image surveillance system enters into a surveillance state.

Detecting a vehicle that enters into search region, where upon the monitoring device automatically enters into an occupancy mode, and performs a data acquisition process for gamma and neutron detection in accordance with the time required by an alarm algorithm, so as to obtain a respective total count rate.

Detecting the times T1 and T2 for the vehicle when it reaches the two points with a distance L, and calculating the vehicle's speed V.

Setting an alarm threshold by using an algorithm based upon the background count rate updated in real time, and sending an alarm signal when the total count rate exceeds the alarm threshold.

Transmitting the alarm signal to the image surveillance system via a control interface to notify the image surveillance system to start recording. Additionally, an alarm command is sent to an audio and visual alarm system to inform it to send out an alarm.

With the help of the results of radioactivity detection, speed detection and image capturing, a local computer can specify the position where the radioactive material(s) are located with methods of horizontal and vertical positioning.

According to the method above described, the image surveillance system can save the images recorded 30 seconds before starting to record. Additionally, the horizontal positioning can calculate the horizontal distance, $S=V\times(T_s-T_1)$, between the radioactive material(s) and the head of the vehicle on the basis of the time Ts when the ray detector detects that radioactive material(s) is (are) passing through the search region.

According to the method described above, the vertical positioning is realized according to the difference in the count rates obtained from the two or three groups of radioactivity detectors preset in the vertical direction. In some embodiments, at least two groups of radioactivity detectors are employed to calculate the vertical positioning.

In some embodiments, a device implementing the above method can include pedestals symmetrically preset on both sides of, for example, a road, wherein each pedestal includes one or more ray detectors, an electronic control box and audio and visual alarm units mounted on the pedestals. The pedestals can further include pick-up heads of the image surveillance system mounted on the pedestals, and speed detectors mounted on, for example, both sides of the bottom of the pedestals and a local computer.

In the above device, the ray detectors can include gamma ray detectors and neutron ray detectors.

In the above device, several groups of the gamma ray detectors and neutron ray detectors can be arranged vertically on, for example, the inner sides of the pedestals.

Compared with existing techniques, the present invention, with the help of the newly added functions of speed detection and image surveillance, as well as the help of the methods of horizontal and vertical positioning, can easily and quickly specify the vehicle and the exact position of the radioactive material(s), so that the radioactive material(s) can be conveniently isolated and processed. In this way, time spent on detection can be reduced, which can save time and money.

A further explanation on detailed implementation of the present invention will be described with the help of the drawings.

DETAILED DESCRIPTION OF THE PREFERRED EMBODIMENTS

Figure 1:
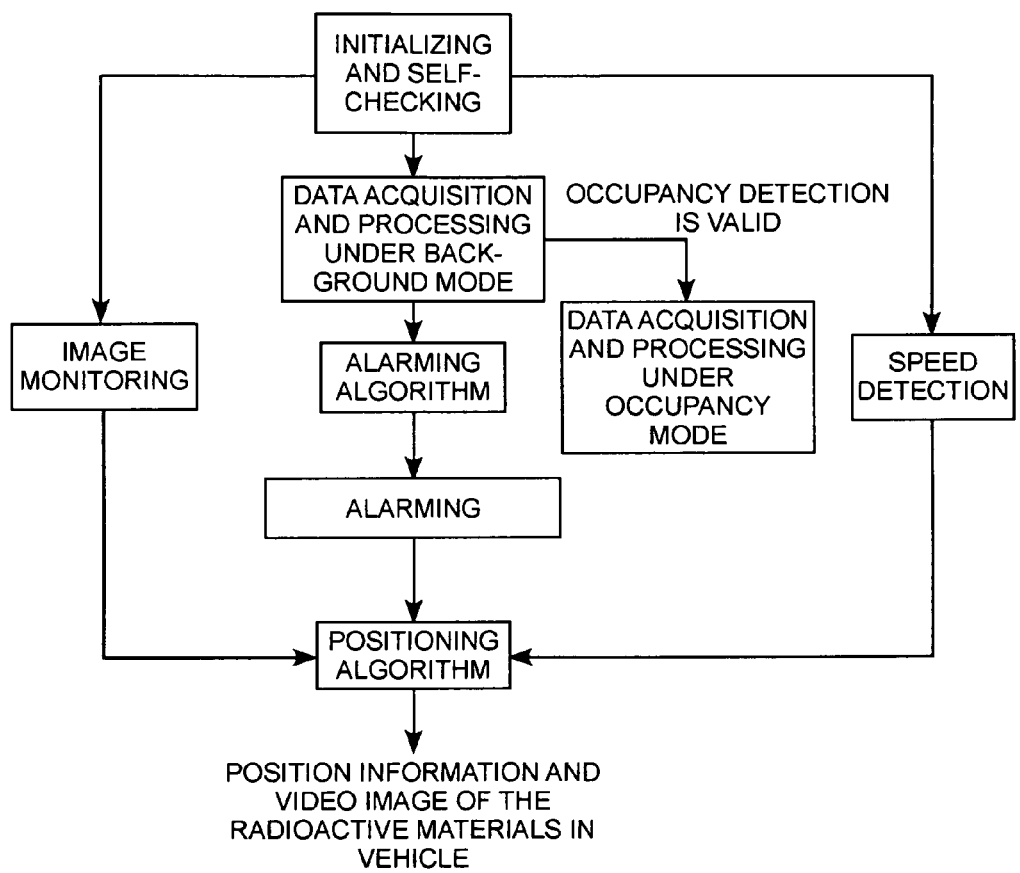
FIG. 1 is a flow chart of a technical solution according to the present invention.
Figure 2:
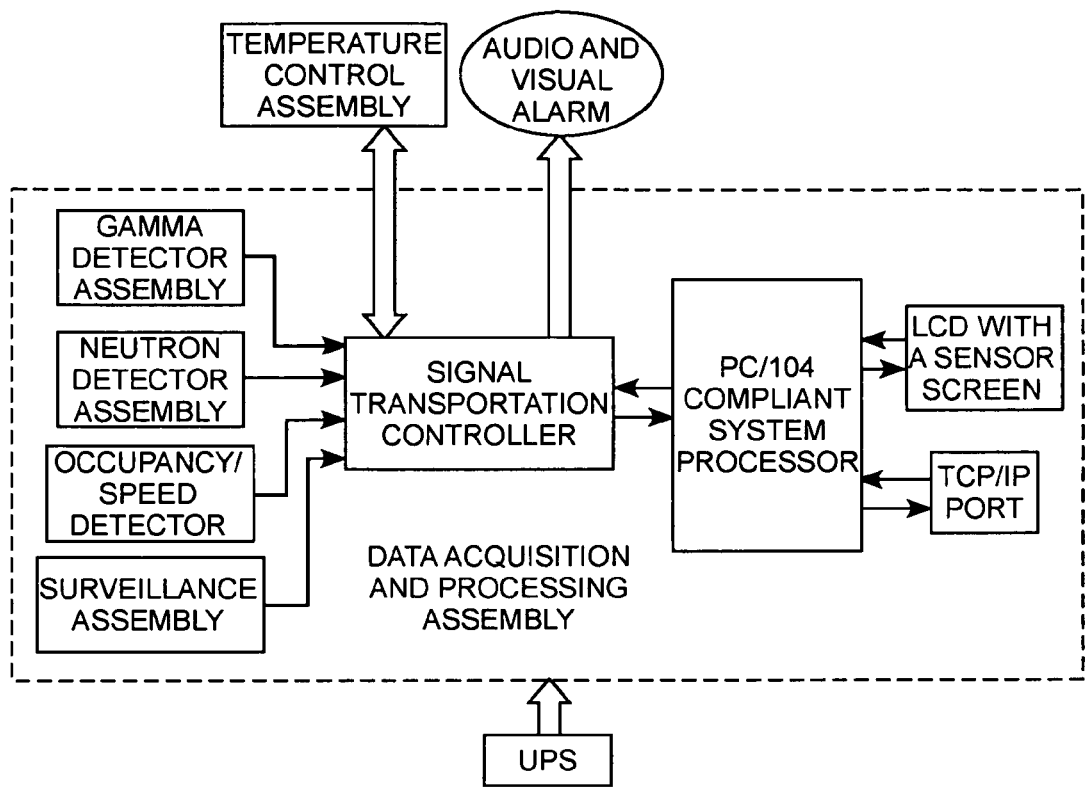
FIG. 2 is a systemic configuration diagram of the present invention.
Figure 3:
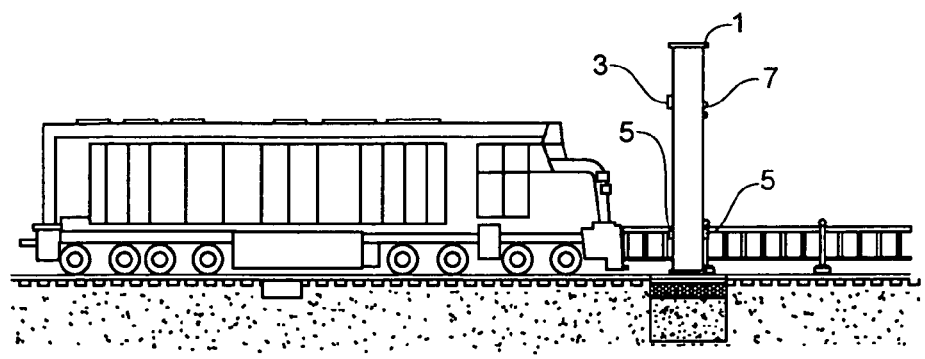
FIG. 3 is an application status diagram of the present invention.
Figure 4:
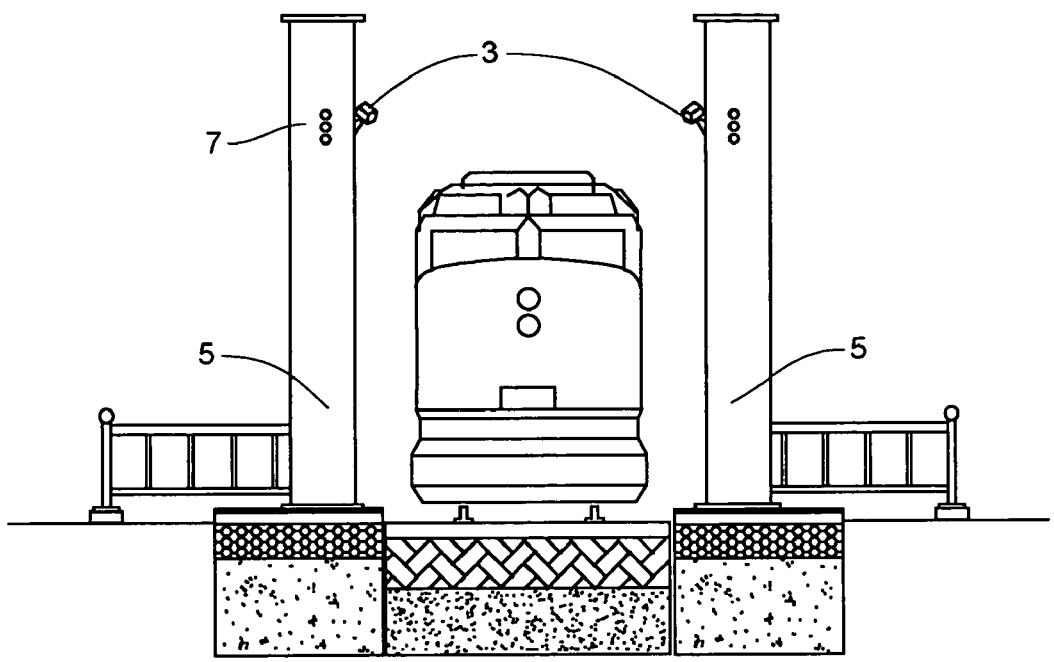
FIG. 4 is the right side view of FIG. 3.
Figure 5:
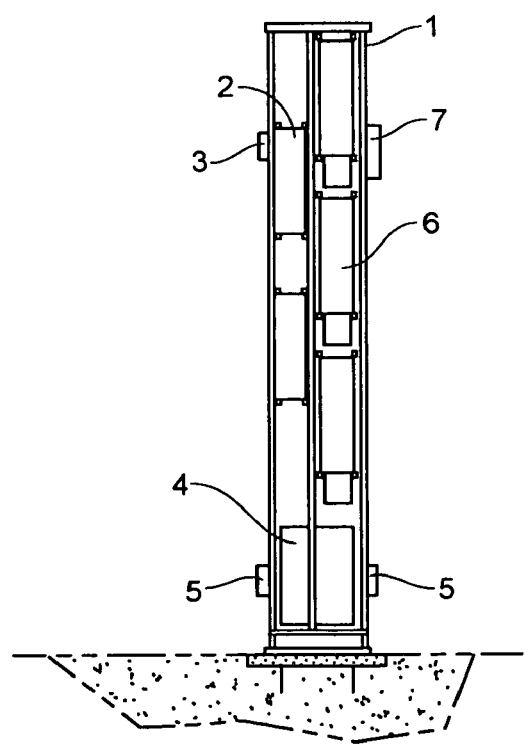
FIG. 5 is a schematic diagram of the inner sides of the pedestal of the present invention.
Figure 6:
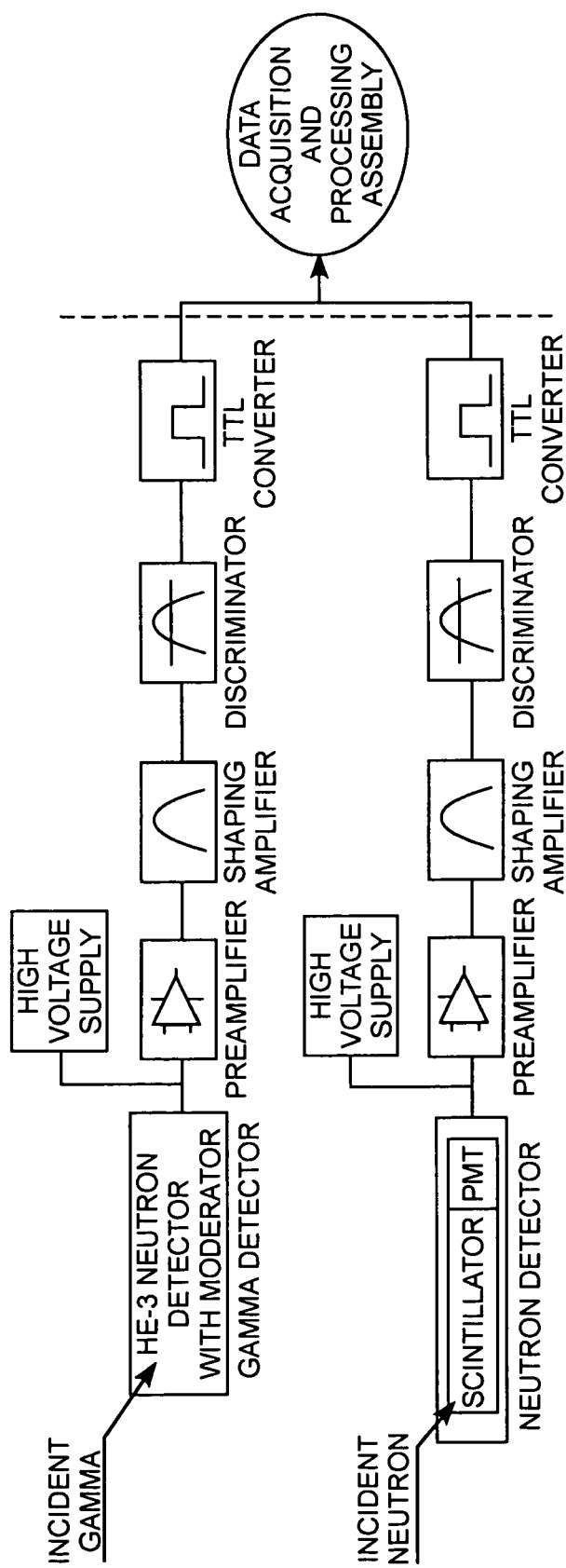
FIG. 6 shows a concept diagram of a detector circuit of the present invention.

As depicted in FIGS. 2-5, a device for implementing the present invention can comprise pedestals 1 symmetrically preset on both sides of a road. The pedestals can include one or more neutron rays detectors 2, one or more gamma ray detectors 6, an electronic control box 4, an audio and visual alarm 7, pick-up head 3, occupancy/velocity detector 5 and a local computer. The specific implementation includes following steps:

Power on the monitoring device of the present invention. The ray detector, i.e. neutron ray detector 2 and gamma ray detector 6, can enter into a detection state. After initializing and self-checking, the device of the invention automatically enters into a process of background acquisition, and the pick-up 3 enters into surveillance state. An embodiment of a detector circuit is shown in FIG. 6. Gamma and neutron rays leaked from a radioactive source can enter into the ray detector and part of the energy of the rays can be converted into electronic impulse signals to output. The output signals from the photo-multiplier in the gamma detector and the $^3$He-neutron tube in the neutron detector are amplified by a preamplifier and shaped by a shaping amplifier. The pulse height discriminators are calibrated to form a region of interest containing radioactive materials radiation. The discriminated signals are converted into standard TTL impulse signals so that the sequent data acquisition and processing assembly can perform data acquisition.

Figure 7:
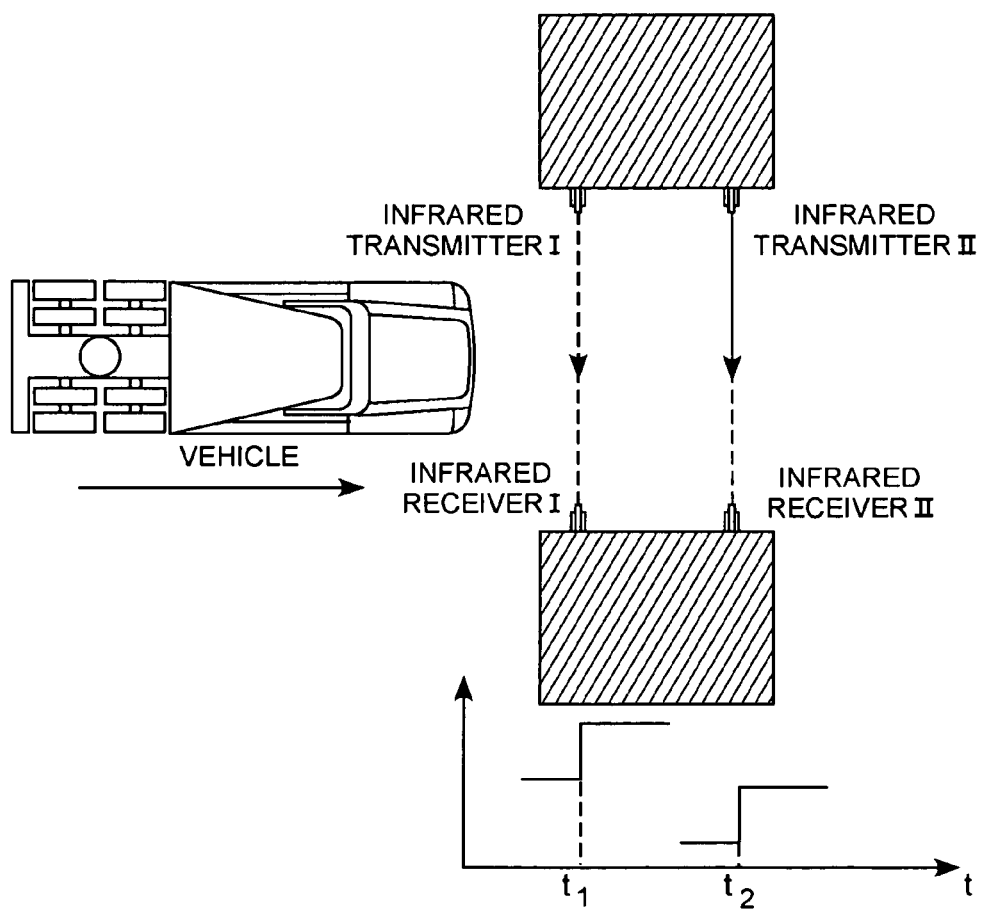
FIG. 7 schematically shows an implementation of the velocity detecting in the present invention.

As can be seen from FIG. 7, occupancy/speed detector 5 can comprise two pairs of infrared transmitters and infrared receives. When the vehicle is passing through the detecting channel, the occupancy/speed detector 5 will be triggered. At this time, the device of the present invention enters into occupancy mode, and perform data acquisition process for gamma and neutron detection under the occupancy mode in accordance with the time required by the alarm algorithm, so as to obtain respective total count rates.

Speed detector 5 can be composed of the infrared speed-detecting device I and the infrared speed-detecting device II. By the photo-electronic converting function of the infrared receiver, it converts the information on speed of the desired vehicle into electronic impulse signals having corresponding time information. When a vehicle passes through the infrared speed-detecting device I of the speed detector 5, the infrared speed-detecting device I can generate an impulse response and records the time T1 when the impulse response is generated. Similarly, when the vehicle passes through the infrared speed-detecting device II of the speed detector 5, the infrared speed-detecting device II can generate an impulse response and records the time T2 when the said impulse response is generated. Because we know the distance between the two infrared speed-detecting devices as L, and L is considerably small, we can suppose that the vehicle's motion within the said distance be uniform, the vehicle's speed V=L/(T2−T1) can be calculated.

An alarm threshold is obtained by using an algorithm on the basis of alarm algorithm, particularly, the background count rate updated in real time, and an alarm signal can be sent when the total count rate exceeds the alarm threshold.

The alarm threshold can be obtained on the basis of the principle of ray detection statistics with the following formula:

$$BKG+NSIGMA\sqrt{BKG}$$

wherein BKG denotes background count rate and NSIGMA denotes a statistics coefficient, which can be adjusted according to the detection reliability and false alarm rate.

The number of impulse recorded during a unit time is called count rate. Besides rays leaking from radioactive materials, cosmic rays, which continuously bombard the atmosphere, and natural radiation materials existing in the environment can cause the similar counts. Count rate caused by other particles, except the rays leaking from radioactive materials, are defined as background count rate, while count rate caused by leaking rays from radio active material is net count rate. The sum of them is total count rate.

The alarm signal can be transmitted to the pick-up head 3 of the image surveillance system via a control interface to notify it to start recording. Additionally, the pick-up head 3 can save the images recorded 30 seconds before starting record. Furthermore, an alarm command can be sent to the audio and visual alarm unit 7 to inform it to send out an alarm.

With the help of the results of radioactivity detection, speed detection and image capturing, the local computer carries out the horizontal positioning process on the radioactive materials.

If the vehicle under the test is rather short, identification can be done by extracting the image of the vehicle passing through at the time Ts (this time is detected by the ray detector) from the continuous ones recorded by the pick-up head 3 of the image surveillance system.

However, if the vehicle's body is very long, according to the starting time T1 provided by the speed detector when the vehicle comes to the visual field of the speed detector, and the vehicle's calculated speed at this time, and the time Ts when ray detector detects that the radioactive substance is passing through, we can obtain the radioactive substance lactation a distance S=V×(Ts−T1) from the head of the vehicle in horizontal direction.

Additionally, for the double-deckers, it can be desirable to specify whether the substances are hidden in the upper or in the lower compartments. In this case, vertical positioning on the radioactive materials can be implemented with the local computer according to the results of radioactivity detection, speed detection and image capturing. In the implementation of the vertical positioning, two or three groups of gamma ray detectors 6 and neutron ray detectors 2 are adopted and arranged in two groups vertically. When the radioactive materials pass through in different heights, the count rates detected by gamma ray detectors 6 and the neutron ray detectors 2 in the vertical direction are different. According to the difference of each group of radioactivity detectors, the vertical positioning can be accomplished.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. A method for monitoring the position of radioactive materials in vehicles, comprising the steps of:
    powering on a monitoring device, wherein after initializing, the device automatically enters into background mode to acquire and process gamma and neutron detection data so as to obtain and update a background count rate in real time, and wherein an image surveillance system enters into a surveillance state;

detecting a vehicle that enters into a monitoring channel, where upon the monitoring device automatically enters into an occupancy mode and performs a data acquisition process for gamma and neutron detection in accordance with the time required by an alarm algorithm so as to obtain respective total count rates;

detecting times T1 and T2 for the vehicle when it reaches two points with a distance L, and then calculating the vehicle's speed V using T1, T2 and L;

setting an alarm threshold based upon the updated background count rate, and sending an alarm signal when the total count rate exceeds the alarm threshold;

transmitting the alarm signal to an image surveillance system via a control interface to notify the image surveillance system to start recording, and sending an alarm command to an audio and visual alarm system to send out an alarm;

locating the position where the radioactive material is located using methods of horizontal and vertical positioning using the calculated speed.

2. The method for monitoring the position of radioactive materials in vehicles as claimed in claim 1, wherein the image surveillance system can save the images recorded 30 seconds before starting to record.

3. The method for monitoring the position of the radioactive materials in vehicles as claimed in claim 1, wherein the horizontal positioning calculates a horizontal distance between the radioactive material and the head of the vehicle at the time Ts when the ray detector detects radioactive material.

4. The method for monitoring the position of radioactive materials in vehicles as claimed in claim 3, wherein the vertical positioning is realized according to the difference in the count rates obtained from at least two of radioactivity detecting modules preset in the vertical direction.

5. A device for implementing the method for monitoring the position of radioactive materials in vehicles of claim 1 comprising pedestals symmetrically preset on opposite sides of a road, wherein each pedestal comprises a ray detector, an electronic control box, an audio and visual alarm pickup heads of an image surveillance system, a speed detector and a local computer, and wherein the ray detector, the electronic control box, the audio and visual alarm, the speed detector and the pick-up heads are all operably coupled to the local computer.

6. The device as claimed in claim 5, wherein said ray detector includes a gamma ray detector and neutron ray detector.

7. The device as claimed in claim 6, wherein a plurality of groups of said gamma ray detector and neutron ray detector are arranged vertically on the each pedestal.

* * * * *